United States Patent
Fabian et al.

[11] Patent Number: 5,233,987
[45] Date of Patent: Aug. 10, 1993

[54] SYSTEM AND METHOD FOR MONITORING PATIENT'S COMPLIANCE

[75] Inventors: Liboslav Fabian, New Brighton; Alexander Kipnis, New Hope, both of Minn.

[73] Assignee: Empi, Inc., St. Paul, Minn.

[21] Appl. No.: 911,128

[22] Filed: Jul. 9, 1992

[51] Int. Cl.[5] ............................................ A61B 10/00
[52] U.S. Cl. .................................. 607/41; 128/774; 128/778; 607/115
[58] Field of Search ............... 128/419 R, 420 R, 421, 128/422, 419 PT, 783, 774, 778, 738; 364/413.02, 413.27

[56] References Cited

U.S. PATENT DOCUMENTS

| | | | |
|---|---|---|---|
| 3,933,147 | 1/1976 | DuVall et al. | 128/421 |
| 4,515,167 | 5/1985 | Hochman | 128/738 |
| 4,642,769 | 2/1987 | Petrofsky | 364/413.27 |
| 4,712,179 | 12/1987 | Heimer | 128/419 PT |
| 4,738,268 | 4/1988 | Kipnis | 128/775 |
| 4,817,044 | 3/1989 | Ogren | 364/413.02 |
| 4,832,033 | 5/1989 | Maher et al. | 128/421 |
| 5,088,056 | 2/1992 | McIntosh et al. | 364/413.02 |

Primary Examiner—Kyle L. Howell
Assistant Examiner—George Manuel
Attorney, Agent, or Firm—Kinney & Lange

[57] ABSTRACT

A medical patient's compliance with a prescribed regimen of treatment is monitored through elapsed time of equipment operation. A treatment device used by the patient applies a stimulation signal to the patient through an electrode and counts a first clock signal which produces a first count indicative of the length of time which the stimulation signal is applied. When the patient revisits the doctor, a compliance monitor readout device is connected to the treatment device to facilitate the compliance monitoring. The treatment device then counts, in response to second clock signal generated by the compliance monitor, from the first count to a second predetermined count. The compliance monitor readout device also counts the second clock signal and produces a third count. The compliance monitor readout device then displays an output as a function of the third count.

20 Claims, 4 Drawing Sheets

SYSTEM AND METHOD FOR MONITORING PATIENT'S COMPLIANCE

BACKGROUND OF THE INVENTION

The present invention relates to a system and method for measuring and monitoring elapsed time. In particular, medical patient compliance with a prescribed regimen of treatment is monitored through elapsed time of equipment operation.

Millions of women suffer from urinary incontinence, which is the inability to retain urinary discharge. It has long been known that strengthening the muscles of the pelvic floor and urinary sphincter can be achieved through the use of the Kegel exercise. A patient who performs the Kegel exercise will repeatedly and voluntarily contract and relax the pelvic musculature for a predetermined length of time.

In spite of proven effectiveness of the Kegel exercise when practiced faithfully, this treatment has often failed because of lack of patient compliance. Exercises not properly completed will not yield satisfactory results. The tendency is to give up and learn to live with the problem.

Another option for women with urinary incontinence is to pursue more aggressive treatment alternatives such as drug therapy or surgery. These approaches, however, have had limited effectiveness over time.

Still another option is the use of electrical neuromuscular stimulation. It has been shown that electrical neuromuscular stimulation of dysfunctional muscles by means of a vaginal electrode can effectively prevent the unwanted flow of urine. Nerve fibers are electrically stimulated by means of transcutaneously applied pulses of electrical current to cause contraction of the dysfunctional muscle. Furthermore, through the use of such an electrode some patients can educate themselves to voluntarily or automatically impede the flow of urine.

It is often advantageous to be able to measure elapsed time of operation of equipment. Particularly in medicine, it is useful for a doctor to know how well a patient is complying with a prescribed regimen of treatment in order to be able to judge the treatment's efficiency.

A typical compliance monitor system might consist of a treatment detector, a treatment time counter, and a readout device. These are used, respectfully, to detect that a treatment is being used in an acceptable fashion, to count the time interval of the treatment, and to display and clear the treatment time counter reading.

When the readout device is separate from the treatment time counter, which is often the case in portable treatment devices, it is necessary to provide means of connecting the two in order to utilize the display and clear functionality. It is often desired to minimize the number of signal lines used for such connection for reasons of cost, size, and reliability.

There are prior references which discuss methods of storing and retrieving data related to a patient's use of a medical device. Petrofsky, U.S. Pat. No. 4,642,769, entitled METHOD AND APPARATUS FOR PROVIDING STIMULATED EXERCISE OF PARALYZED LIMBS, discloses a computer controlled system for controlling precise movement of paralyzed muscles through electrical stimulation. A physician programs a memory cartridge which is used by the patient at remotely located and computer controlled exercise equipment. The cartridge stores records of the intensity and length of a work out. The cartridge can record specific exercise data, such as a leg lift count, by incrementing the data in a memory location each time the leg is lifted. The exercise is automatically terminated after the count exceeds a prescribed maximum number. The physician can recall the data directly from the cartridge.

Kipnis, U.S. Pat. No. 4,738,268, entitled RELATIVE CLOCK TIME, discloses a time clock for determining the relative time between two or more events independently of wall clock time. Each time a patient begins recording data, stops recording data, or presses a separate button to indicate the patient believes a certain event is taking place, a time stamp is added to the data. This data is then recorded as digital information. After the recording is complete, the data is transferred to a physician through a modem.

Ogren, U.S. Pat. No. 4,738,268, entitled COLLECTION AND REPORTING SYSTEM FOR MEDICAL APPLIANCES, discloses a data collection and reporting system for medical appliances. The system includes a usage monitor device which is attached to a host medical instrument. The meter automatically logs clock times when the instrument is turned on or off. The meter includes an electronical flag indicator which indicates meter overflow. The meter flashes the flag indicator at a six month point to indicate the need for preventative maintenance. A portable data collector collects the data from the monitoring device through an eight pin telephone type cable.

Maher et al., U.S. Pat. No. 4,832,033, entitled ELECTRICAL STIMULATION OF MUSCLE, discloses an electrical stimulation system having a system controller and a personal, portable stimulator unit. The stimulator unit is programmed to store in its memory the characteristics of the applied stimulation patterns and a record of the number of times that the patient has applied them. Maher et al. discloses several interfaces between the system controller and the personal unit. In each of these configurations, the information is stored and transferred as a digital word.

Each reference discloses methods of storing and retrieving data related to a patient's use of a medical device. However, in each of these methods, the data is stored and transferred as a digital word. The equipment used to transfer this data is thus both bulky and expensive.

SUMMARY OF THE INVENTION

The present invention provides an inexpensive circuit for measuring and monitoring medical patient compliance (i.e. elapsed time of equipment operation) while also minimizing the size of the portable treatment device which the patient maintains.

To measure and monitor a patient's compliance with a prescribed regimen of treatment, the patient carries a portable treatment device. The treatment device has a binary counter, called a treatment time counter, which utilizes a treatment timebase clock source connected to its input in order to count elapsed treatment time. The binary counter is enabled by a treatment detector which detects current applied to the patient via an electrode. When a treatment is being used in an acceptable fashion the current applied to the patient must be above a threshold value of approximately 10 mA plus or minus 30 percent (30%) for the treatment detector to provide an indication to the binary counter.

In the present invention, when a doctor wishes to determine a patient's compliance with the prescribed regimen of treatment, the patient returns the treatment device to the doctor. The doctor then plugs a readout device into the treatment device. A readout timebase, which is a clock source located in the readout device and is of much higher clock rate than the treatment timebase clock rate, is connected both to the binary counter input of the treatment device and to a readout counter located in the readout device. The readout timebase clock source causes the treatment time counter to count up, while at the same time a readout counter will count the same clock source down from a predetermined initial value utilizing a predetermined prescaling factor.

When the treatment time counter reaches a maximum count, an overflow signal from the treatment time counter is detected and the readout timebase is disabled. The readout counter will contain a value representative of the elapsed equipment time which is latched and displayed in a readout display. At the same time, the overflow signal also resets the treatment time counter.

The elapsed equipment time displayed by the readout device allows the doctor to determine whether the patient has complied with the prescribed treatment.

DETAILED DESCRIPTION OF THE PREFERRED EMBODIMENTS

Figure 1:
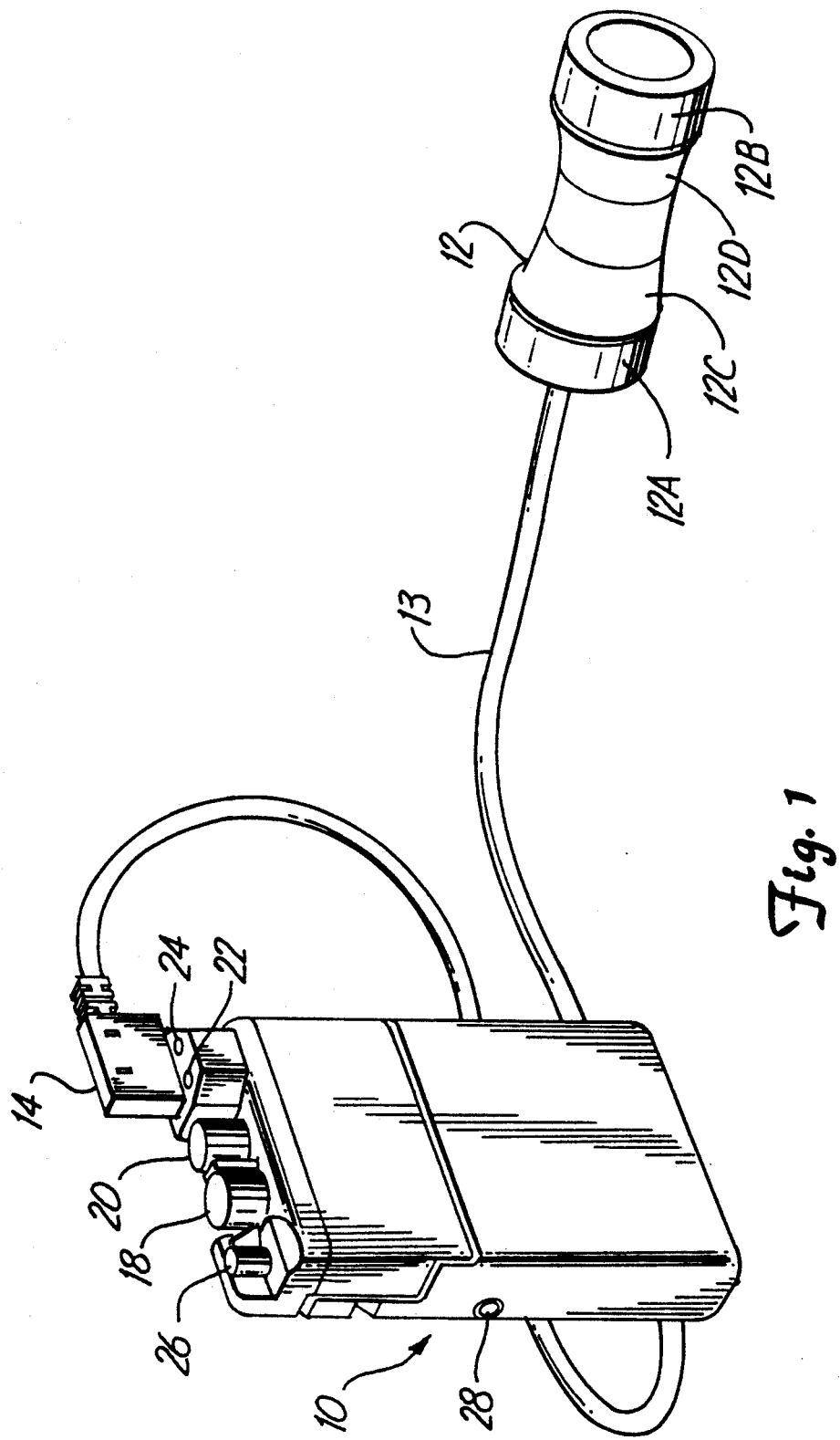
FIG. 1 shows a treatment device and a treatment electrode.

A portable patient treatment device 10 and treatment electrode 12 are shown in FIG. 1. Portable patient treatment device 10 includes plug 14, port 16 (shown in FIG. 2), first channel control 18, second channel control 20, operation lights 22 and 24, timed treatment control 26, and port 28.

During operation, treatment electrode 12 is connected to portable patient treatment device 10 by cable 13. Plug 14 is connected into port 16 (shown in FIG. 2). For patient stimulation, treatment electrode 12 is inserted into a woman's vagina while plug 14 is connected to portable patient treatment device 10 via port 16 (shown if FIG. 2).

Treatment electrode 12 is a two-channel device. It has a first pair of electrodes 12A, 12B and a second pair of electrodes 12C, 12D. First and second channel controls 18 and 20 control the electrical stimulation signals supplied to first electrode pair 12A, 12B and second electrode pair 12C, 12D, respectively. Operation light 22 indicates when the first channel is in operation, while operation light 24 indicates when the second channel is in operation. Timed treatment control 26 provides the option of running the patient stimulation for various intervals with automatic shut off. Port 28 allows portable patient treatment device 10 to interact with compliance monitor readout device 30 (shown in FIG. 2). Compliance monitor readout device 30 is normally kept at a doctor's office.

Figure 2:
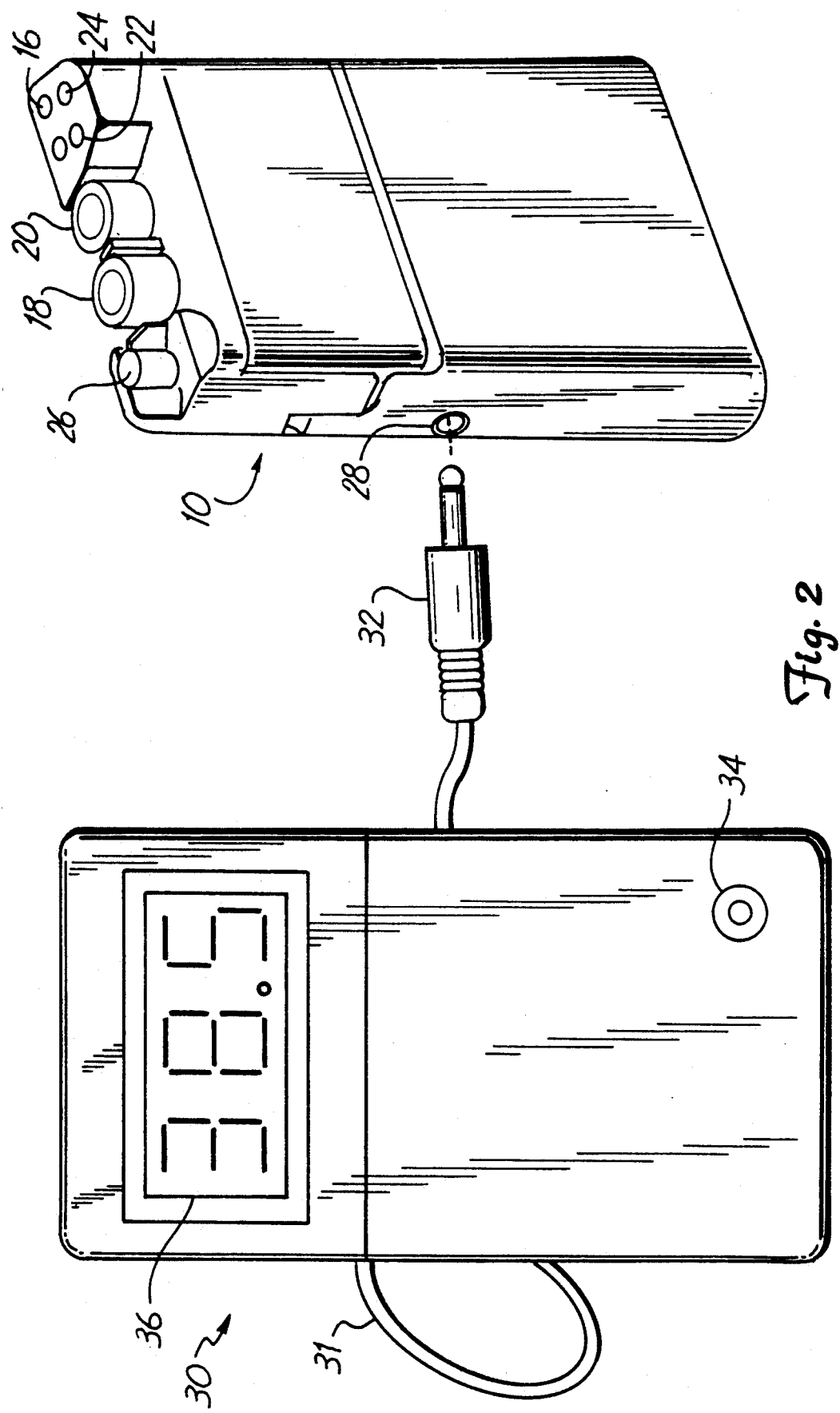
FIG. 2 shows the treatment device and a readout device connected to one another.

FIG. 2 shows portable patient treatment device 10 and compliance monitor readout device 30. Compliance monitor readout device 30 includes cable 31, plug 32, pushbutton 34, and display 36.

Compliance monitor readout device 30 interprets and displays data stored in portable patient treatment device 10. This interpretation is done by first connecting plug 32 of compliance monitor readout device 30 into port 28 of portable patient treatment device 10. The doctor then pushes push button 34. After a short pause, readout display 36 displays the elapsed time of treatment.

Figure 3:
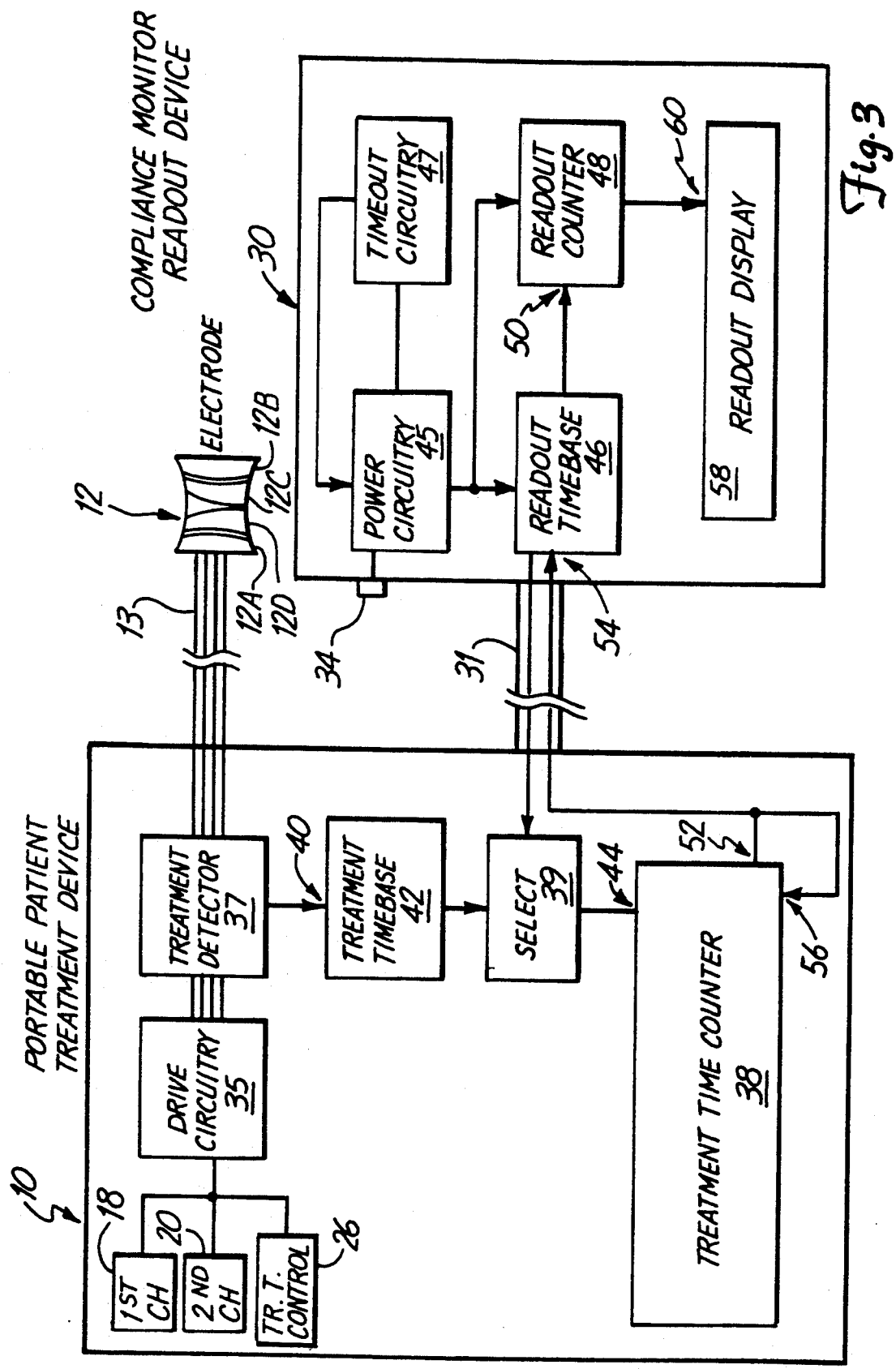
FIG. 3 is a block diagram of both the treatment device and the readout device.

FIG. 3 is a block diagram which shows portable patient treatment device 10, electrode 12, and compliance monitor readout device 30. Portable patient treatment device 10 includes first channel control 18, second channel control 20, timed treatment control 26, drive circuitry 35, treatment detector 37, treatment time counter 38, select circuitry 39, and treatment timebase 42. Compliance monitor readout device 30 contains push button 34, power circuitry 45, readout timebase 46, timeout circuitry 47, readout counter 48, and readout display 58.

First and second channel controls 18 and 20 and time treatment control 26 control drive circuitry 35. Drive circuitry 35 provides power to treatment detector 37.

Treatment detector 37 monitors current through electrode 12 via cable 13. Treatment detector 37 also enables treatment timebase 42 through enable 40. The patient current provided to electrode 12 must be above a threshold value of approximately 10 mA plus or minus thirty percent (30%) for treatment detector 37 to provide an indication to treatment timebase 42.

Select circuitry 39 selects signals (i.e., clock pulses) from either treatment timebase 42 or readout timebase 46 of compliance monitor readout device 30. Select circuitry 39 then provides these selected clock pulses to treatment time counter 38 through treatment time counter input 44.

When a doctor wishes to determine patient compliance with a prescribe regimen of treatment, the patient returns portable patient treatment device 10 to the doctor. The doctor then interconnects compliance monitor readout device 30 with portable patient treatment device 10 via cable 31. Plug 32 (shown in FIG. 2) of compliance monitor readout device 30 is plugged into port 28 (shown in FIG. 2) of portable patient treatment device 10. The doctor then pushes push button 34 of compliance monitor readout device 30.

When the doctor pushes push button 34, power circuitry 45 powers readout timebase 46, timeout circuitry 47, and readout counter 48.

Readout timebase 46 provides clock pulses both to read counter 48 through readout counter clock input 50 and to select circuitry 39. The clock pulse provided by readout timebase 46 is a high frequency clock rate, such as 2 megaHertz. Treatment time counter 38, which is a binary counter, counts up at this high frequency rate while readout counter 48 counts down at the same high frequency rate from a predetermined initial value utilizing a predetermined scaling factor.

The following formula describes the setting of the predetermined initial value of readout counter 48:

$$IVRC = TTCMC/TTCR, \text{ where}$$

IVRC is the Initial Value of Readout Counter 48,
TTCMC is the Maximum Count of Treatment Time Counter 38, and
TTCR is the Clock Rate of Treatment Timebase 42.

In one preferred embodiment, the following values were found to work well:

TTCMC = $2^{23}$, or 8,388,608

TTRC = 37.5 Hz, or 13,500 counts per 0.1 hour interval

IVAC = 622 (counting 62.2 hours in 0.1 hour increments).

The predetermined scaling factor of readout counter 48 is determined by the following formula:

SFRC = TTCR·DTU, where

SFRC is the Scaling Factor of Readout Counter 48, TTCR is the Clock Rate of Treatment Timebase 42, and DTU is the Displayed Time Unit in seconds.

In one preferred embodiment, the following values were found to work well:

TTRC = 37.5 Hz, or 13,500 counts per 0.1 hour interval

DTU = 360 seconds per 0.1 hour

SFRC = 13,500.

When treatment time counter 38 reaches a maximum, preset count, an overflow signal is detected and sent from overflow 52 of treatment time counter 38 to both disable 54 of readout timebase 46 and reset 56 of treatment time counter 38. Treatment time counter 38 is thus reset.

As this point, readout counter 48 contains a value representative of elapsed treatment time which is latched. Readout counter 48 then enables readout display 58 through enable 60. Readout display 58 displays the elapsed treatment time.

After a fixed time interval in which there has been a proper reading and display of elapsed treatment time, such as one minute, timeout circuitry 47 turns compliance monitor readout device 30 off by disabling power circuitry 45. If push button 34 is pushed and there is an improper reading, timeout circuitry 47 will turn compliance monitor readout device 30 off by disabling power circuitry 45 after a shorter fixed time interval, such as ten seconds.

Figure 4:
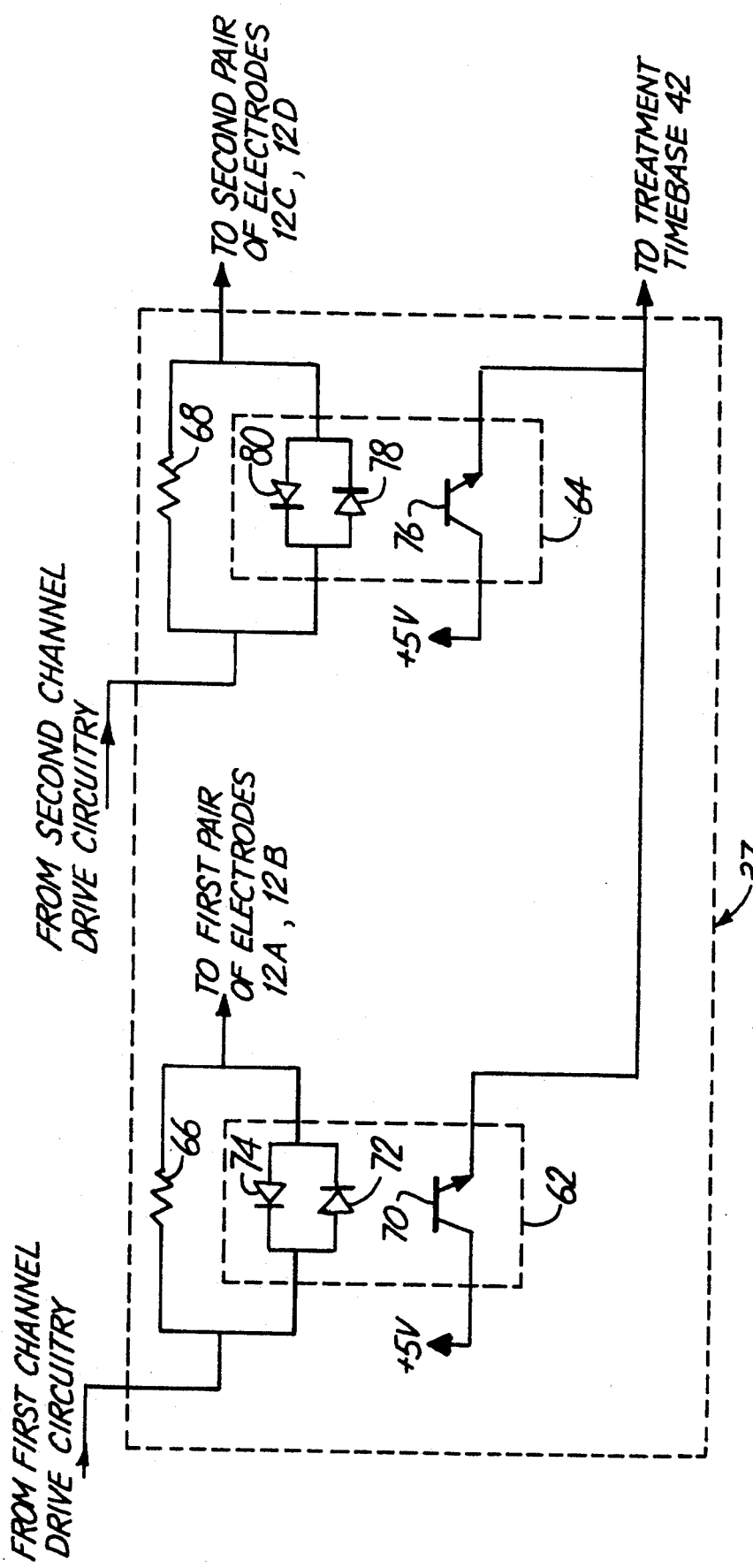
FIG. 4 is a schematic of a treatment detector.

FIG. 4 is a schematic diagram of treatment detector 37. Treatment detector 37 includes first bidirectional optocoupler 62, second bidirectional optocoupler 64, resistor 66, and resistor 68. First bidirectional optocoupler 62 consists of phototransistor 70 and light emitting diodes (LEDs) 72 and 74. Second bidirectional optocoupler 64 includes phototransistor 76 and light emitting diodes (LEDs) 78 and 80.

First bidirectional optocoupler 62 and resistor 66 receive input from driver circuitry 35. LED 72, LED 74, and resistor 66 are connected in parallel. Neither LED 72 nor LED 74 is forward biased until the forward voltage is approximately 0.9 volts. This forward voltage remains relatively constant with changes in forward current. Thus, LED 72 or LED 74 will not turn on until the current through resistor 66 is sufficient to cause a voltage drop across it equal to 0.9 volts. By setting the value of resistor 66 in the range of 90 to 120 ohms, LEDs 72 and 74 will turn on when the stimulator output current to the first pair of electrodes 12A and 12B is approximately 10 milliamps or higher.

Bidirectional optocoupler 64 and resistor 68 function identically to bidirectional optocoupler 62 and resistor 66. However, bidirectional optocoupler 62 and resistor 66 function relative to the current supplied to first pair of electrodes 12A and 12B, while second bidirectional optocoupler 64 and resistor 68 function relative to current supplied to second pair of electrodes 12C and 12D.

The emitters of phototransistor 70 and phototransistor 76 are interconnected before transmitting an output to treatment timebase 42. Therefore, it is sufficient for either one of the output channels to have a current above the threshold of 10 milliamps to transmit an output to treatment timebase 42.

In summary, the present invention provides a simple and inexpensive way of monitoring patient compliance in using an electrical stimulation treatment device.

Although the present invention has been described with reference to preferred embodiments, workers skilled in the art will recognize that changes may be made in form and detail without departing from the spirit and scope of the invention.

What is claimed is:

1. A method for monitoring a patient's compliance with a treatment program, the method comprising:
   treating a patient with a treatment device by:
      applying a stimulation signal to an electrode;
      detecting, in a treatment detector, electrode stimulation above a current threshold;
      selecting a treatment time counter input from at least one clock signal;
      counting, in a treatment time counter, a first clock signal, which is produced when the treatment detector detects electrode stimulation above the current threshold to produce a first count indicative of the length of time which the stimulation signal is applied;
   monitoring patient compliance with a compliance monitor readout device by:
      connecting the compliance monitor readout device to the treatment device;
      counting, in the treatment time counter, in response to a second clock signal supplied by the compliance monitor readout device, from the first count to a second predetermined count;
      counting, in the compliance monitor readout device, in response to the second clock signal while the treatment time counter counts from the first count to the second count, to produce a third count; and
      displaying an output on a readout display as a function of the third count.

2. The method of claim 1 wherein the stimulation signal is an electrical signal within a frequency range of 5 Hz to 75 Hz.

3. The method of claim 1 wherein the stimulation signal consists of a first stimulation signal portion and a second stimulation signal portion.

4. The method of claim 3 wherein the levels of the first and second stimulation signal portions are within a frequency range of 5 to 75 Hz.

5. The method of claim 1 wherein the treatment detector consists of a first optocoupler, a second optocoupler, a first resistor, and a second resistor.

6. The method o claim 5 wherein the first optocoupler and the first resistor are connected in parallel and the second optocoupler and the second resistor are connected in parallel.

7. The method of claim 6 wherein the first and second optocouplers are connected in parallel.

8. The method of claim 1 wherein the current threshold is about 10 milliamps.

9. The method of claim 1 wherein the first clock signal is approximately 40 Hz.

10. The method of claim 1 wherein the second clock signal is approximately 2 MHz.

11. A device for monitoring a patient's compliance with a treatment program, the device comprising:
   a treatment device for treating a patient, the treatment device comprising:
      applying means for applying a stimulation signal to the patient;
      a treatment detector for detecting when the stimulation signal applied to the patient is above a current threshold;
      a first clock which provides a first clock signal during a time period in which the treatment detector indicates the stimulation signal applied to the patient is above the current threshold;
      an external port for receiving a second clock signal;
      selecting means for selecting a treatment time counter input signal based upon clock signals;
      a treatment time counter for counting the treatment time counter input signal;
   a compliance monitor readout device for monitoring an elapsed treatment time of use of the treatment device, the compliance monitor readout device comprising:
      a second clock which provides the second clock signal to the treatment time counter;
      a readout counter for counting a readout count in response to the treatment time counter counting the second clock signal; and
      a readout display which displays the elapsed treatment time as a function of the readout count.

12. The device of claim 11 wherein the stimulation signal is an electrical signal within a frequency range of 5 Hz to 75 Hz.

13. The device of claim 11 wherein the stimulation signal consists of a first stimulation signal portion and a second stimulation signal portion.

14. The device of claim 13 wherein the levels of the first and second stimulation signal portions are within a frequency range of 5 Hz to 75 Hz.

15. The device of claim 11 wherein the treatment detector consists of a first optocoupler, a second optocoupler, a first resistor, and a second resistor.

16. The device of claim 15 wherein the first optocoupler and the first resistor are connected in parallel and the second optocoupler and the second resistor are connected in parallel.

17. The device of claim 16 wherein the first and second optocouplers are connected in parallel.

18. The device of claim 11 wherein the current threshold is about 10 milliamps.

19. The device of claim 11 wherein the first clock signal is approximately 40 Hz.

20. The device of claim 11 wherein the second clock signal is approximately 2 MHz.

* * * * *

UNITED STATES PATENT AND TRADEMARK OFFICE
CERTIFICATE OF CORRECTION

PATENT NO. : 5,233,987
DATED : August 10, 1993
INVENTOR(S) : LIBOSLAV FABIAN, ALEXANDER KIPNIS It is certified that error appears in the above-identified patent and that said Letters Patent is hereby corrected as shown below:

Col. 6, line 64, delete "method o", insert --method of--

Signed and Sealed this

Fifteenth Day of March, 1994

*Attest:*

BRUCE LEHMAN

*Attesting Officer*      *Commissioner of Patents and Trademarks*